United States Patent [19]

Hill

[11] 4,098,887
[45] Jul. 4, 1978

[54] PHARMACEUTICAL COMPOSITIONS AND METHODS OF PRODUCING ANTIARTHRITIC ACTIVITY WITH BIS(PYRIDINE)GOLD(1+) SALTS

[75] Inventor: David T. Hill, North Wales, Pa.

[73] Assignee: SmithKline Corporation, Philadelphia, Pa.

[21] Appl. No.: 772,033

[22] Filed: Feb. 25, 1977

[51] Int. Cl.² ............................................. A61K 31/555
[52] U.S. Cl. .................................................... 424/245
[58] Field of Search ........................................ 424/245

[56] References Cited

U.S. PATENT DOCUMENTS

| | | |
|---|---|---|
| 3,676,554 | 4/1972 | McCristy et al. ................... 260/430 |
| 3,718,679 | 2/1973 | McCristy et al. ................... 260/340 |
| 3,718,680 | 2/1973 | McCristy et al. ................... 260/430 |

OTHER PUBLICATIONS

Goolsby et al., *Analytical Chemistry* 40:1978–1983 (1968).

*Primary Examiner*—Stanley J. Friedman
*Attorney, Agent, or Firm*—Joan S. Keps; Richard D. Foggio; William H. Edgerton

[57] ABSTRACT

Pharmaceutical compositions and methods of producing antiarthritic activity with bis(pyridine)gold(1+) salts.

6 Claims, No Drawings

PHARMACEUTICAL COMPOSITIONS AND METHODS OF PRODUCING ANTIARTHRITIC ACTIVITY WITH BIS(PYRIDINE)GOLD(1+) SALTS

This invention relates to new pharmaceutical compositions and methods of producing antiarthritic activity by administering bis(pyridine)gold(1+) salts. These pharmaceutical compositions and methods are, in particular, of use in the treatment of rheumatoid arthritis.

The pharmaceutical compositions of this invention, in dosage unit form, having antiarthritic activity comprise a pharmaceutical carrier and a bis(pyridine)gold(1+) salt of the following formula:

FORMULA I

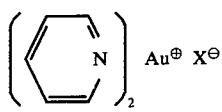

in which X is a weakly nucleophilic anion.

The anion X in Formula I is a weakly nucleophilic anion such as, for example, perchlorate ($ClO_4$), iodate ($IO_4$), tetrafluoroborate ($BF_4$) and hexafluorophosphate ($PF_6$).

The compounds of Formula I are prepared by the following procedure:

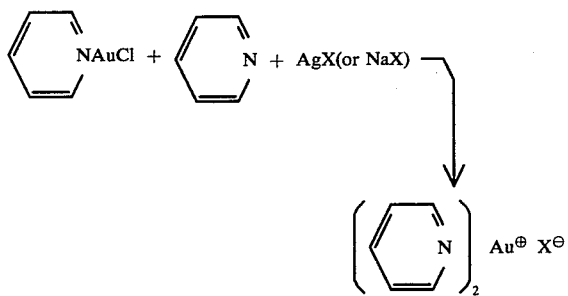

The term X is as defined above.

According to the above procedure, chloro(pyridine)gold(I) is reacted with pyridine and a silver salt AgX or a sodium salt NaX. This reaction is carried out in a solvent, such as acetone, at room temperature. The products are the bis(pyridine)gold(1+) salts of Formula I. These compounds are obtained in solid form.

The chloro(pyridine)gold(I) starting material is known to the art. I have discovered an advantageous process for preparing this compound in which thiodiglycol is reacted with gold acid chloride trihydrate in aqueous ethanol and the resulting solution of chloro[di(2-hydroxyethyl)sulfide]gold(I) is reacted with pyridine to give chloro(pyridine)gold(I).

The bis(pyridine)gold(1+) salts of Formula I are useful in treatment of arthritis. This activity is demonstrated by the following test procedures. Inhibition of adjuvant induced polyarthritis in rats, as measured by reduction of rat paw edema, is produced by compounds of this invention at daily oral doses of about 20 mg./kg. (calculated on gold content). In this test procedure, adjuvant arthritis in rats is produced by a single intradermal injection of 0.75 mg. of *Mycobacterium butyricum* suspended in white paraffin oil into the left hindpaw footpad. The injected paw becomes inflamed (increased volume) and reaches maximal size within 3 to 5 days (primary lesion). The animals exhibit a decrease in body weight gain during the initial period. The adjuvant arthritis (secondary lesion) occurs after approximately 10 days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Antiarthritic activity is shown by the ability to inhibit the development of either primary or secondary lesions of adjuvant arthritis.

The pharmaceutical compositions of this invention are prepared in conventional dosage forms by combining a compound of Formula I in an amount sufficient to produce antiarthritic activity with standard pharmaceutical carriers according to conventional procedures. These procedures may involve mixing, granulating and compressing or dissolving the ingredients as appropriate to the desired preparation. The resulting pharmaceutical compositions are objects of this invention. Oral dosage forms are preferred.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Solid forms for oral administration are preferred. When a solid carrier is used, the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

Preferably, each dosage unit will contain the active ingredient in an amount of from about 1 to about 10 mg.

The pharmaceutical compositions of this invention, in dosage unit forms, exclude simple solutions of the active medicament in solvents which are not conventional solvents used in the preparation of liquid pharmaceutical compositions.

The method of producing antiarthritic activity in accordance with this invention comprises administering internally to an animal a compound of Formula I. The compounds of Formula I are administered in an amount sufficient to produce antiarthritic activity. Usually the active ingredient will be combined with a pharmaceutical carrier. The route of administration may be orally or parenterally, preferably orally. Advantageously, doses will be administered 1 to 2 times a day, with the daily dosage regimen being preferably from about 1 mg. to about 12 mg. When the method is carried out as described above, antiarthritic activity is produced.

One skilled in the art will recognize that in determining the amounts of the active ingredient in the claimed compositions and used in the claimed methods, the activity of the chemical ingredient as well as the size of the host animal must be considered.

The following examples are not limiting but are illustrative of the invention.

EXAMPLE 1

A solution of 3.1 g. (0.025 mole) of thiodiglycol in 5 ml. of ethanol was mixed with a solution of 5.0 g. (0.012 mole) of gold acid chloride trihydrate in 25 ml. of distilled water. The solution was cooled to 0° C. and 10 ml. of pyridine was added. After stirrring for 15 minutes, the precipitate was removed by filtration, washed with water and air dried to give chloro(pyridine)gold(I) which was recrystallized from pyridine-ether.

A solution of 1.33 g. (0.064 mole) of silver perchlorate in 20 ml. of acetone was added to a solution of 2.0 g. (0.064 mole) of chloro(pyridine)gold(I) in 25 ml. of acetone and 25 ml. of pyridine at room temperature. After stirring for 1.5 hours, the solution was filtered and the solvent removed at reduced pressure. The residue was boiled in acetone. Filtering and recrystallizing from pyridine gave bis(pyridine)gold(1+) perchlorate, m.p. 231°–232° C. (dec.).

EXAMPLE 2

Using silver iodate in place of silver perchlorate in the procedure of Example 1 gives bis(pyridine)gold(1+) iodate.

Similarly, using silver tetrafluoroborate gives bis(pyridine)gold(1+) tetrafluoroborate and using silver hexafluorophosphate gives bis(pyridine)gold(1+) hexafluorophosphate.

EXAMPLE 3

| Ingredients | Amounts |
| --- | --- |
| bis(pyridine)gold(1+) perchlorate | 5 mg. |
| magnesium stearate | 5 mg. |
| lactose | 200 mg. |

The above ingredients are screened, mixed and filled into a hard gelatin capsule.

The capsules are administered orally to subjects in need of antiarthritic treatment in amounts within the daily dose range given hereabove.

EXAMPLE 4

| Ingredients | Amounts |
| --- | --- |
| bis(pyridine)gold(1+) perchlorate | 3 mg. |
| calcium sulfate dihydrate | 150 mg. |
| sucrose | 25 mg. |
| starch | 15 mg. |
| talc | 5 mg. |
| stearic acid | 3 mg. |

The bis(pyridine)gold(1+) perchlorate, calcium sulfate dihydrate and sucrose are thoroughly mixed and granulated with 10% gelatin solution. The wet granules are dried, screened and then mixed with the starch, talc and stearic acid and compressed into a tablet.

The tablets are administered orally to arthritic subjects in amounts within the daily dose range given hereabove.

Similarly, the other compounds of Formula I may be formulated into pharmaceutical compositions by the procedures of Examples 3 and 4.

What is claimed is:

1. A pharmaceutical composition, in dosage unit form, having antiarthritic activity comprising a pharmaceutical carrier and in an amount sufficient to produce antiarthritic activity a bis(pyridine)gold(1+) salt of the formula:

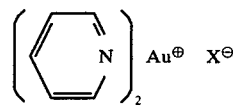

in which X is perchlorate, iodate, tetrafluoroborate or hexafluorophosphate.

2. A pharmaceutical composition of claim 1 in which X is perchlorate.

3. A pharmaceutical composition of claim 1 in a solid form for oral administration.

4. A method of producing antiarthritic activity which comprises administering internally to an animal in an amount sufficient to produce antiarthritic activity a compound of the formula:

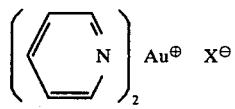

in which X is perchlorate, iodate, tetrafluoroborate or hexafluorophosphate.

5. A method of claim 4 in which X is perchlorate, iodate, tetrafluoroborate or hexafluorophosphate.

6. A method of claim 4 in which X is perchlorate.

* * * * *